United States Patent [19]

Hershberger et al.

[11] Patent Number: 5,470,354
[45] Date of Patent: Nov. 28, 1995

[54] FORCE SENSING APPARATUS AND METHOD FOR ORTHOPAEDIC JOINT RECONSTRUCTION

[75] Inventors: Troy W. Hershberger, Warsaw, Ind.; Robert E. Booth, Jr., Gladwyn, Pa.

[73] Assignee: Biomet Inc., Warsaw, Ind.

[21] Appl. No.: 288,545

[22] Filed: Aug. 10, 1994

Related U.S. Application Data

[63] Continuation of Ser. No. 790,176, Nov. 12, 1991, abandoned.

[51] Int. Cl.$^6$ .................................. A61F 2/38; A61F 2/30
[52] U.S. Cl. ........................ 623/20; 623/18; 606/102; 128/782
[58] Field of Search .............. 623/16–23; 606/86–88, 606/91, 102; 128/782

[56] References Cited

U.S. PATENT DOCUMENTS

| | | |
|---|---|---|
| 3,916,451 | 11/1975 | Buechel et al. . |
| 4,007,495 | 2/1977 | Frazier . |
| 4,206,517 | 6/1980 | Pappas et al. . |
| 4,211,228 | 7/1980 | Cloutier . |
| 4,309,778 | 1/1982 | Buechel et al. . |
| 4,340,978 | 7/1982 | Buechel et al. . |
| 4,353,135 | 10/1982 | Forte et al. . |
| 4,353,136 | 10/1982 | Polyzoides . |
| 4,426,884 | 1/1984 | Polchaninoff . |
| 4,501,266 | 2/1985 | McDaniel . |
| 4,503,705 | 3/1985 | Polchainoff . |
| 4,522,074 | 6/1985 | Hafner . |
| 4,563,778 | 1/1986 | Roche et al. . |
| 4,568,348 | 2/1986 | Johnson et al. . |
| 4,619,658 | 10/1986 | Pappas et al. . |
| 4,624,674 | 11/1986 | Pappas et al. . |
| 4,647,918 | 3/1987 | Goforth . |
| 4,669,302 | 6/1987 | Wagner et al. . |
| 4,673,407 | 6/1987 | Martin . |
| 4,712,542 | 12/1987 | Daniel et al. . |
| 4,795,473 | 1/1989 | Grimes . |
| 4,804,000 | 1/1989 | Lamb et al. . |
| 4,808,186 | 2/1989 | Smith . |
| 4,822,362 | 4/1989 | Walker et al. . |
| 4,834,057 | 5/1989 | McLeod, Jr. . |
| 4,856,993 | 8/1989 | Maness et al. . |
| 4,932,974 | 6/1990 | Pappas et al. . |

(List continued on next page.)

FOREIGN PATENT DOCUMENTS

| | | |
|---|---|---|
| 0346183 | 12/1989 | European Pat. Off. . |
| 0360923 | 4/1990 | European Pat. Off. . |
| 0252762 | 12/1987 | Germany . |
| 3634855 | 3/1988 | Germany . |
| 4019701 | 2/1992 | Germany . |
| 1162727 | 7/1986 | Japan . |
| 0192350 | 2/1967 | U.S.S.R. . |
| 0483594 | 9/1975 | U.S.S.R. . |
| 0963504 | 10/1982 | U.S.S.R. . |

*Primary Examiner*—David H. Willse
*Attorney, Agent, or Firm*—Brooks & Kushman

[57] ABSTRACT

Methods and devices for assessing and determining proper alignment and placement of implant components during joint reconstruction surgery, particularly in the knee joint. Provisional components with force transducers 150, 240 are positioned in the joint 40 and used to determine the precise forces and decide how to balance the forces in the joint. In the knee joint, a provisional tibial component 80 and a provisional patella component 85 are used. The tibial component has a base member 84 and a pair of bearing elements 88, 90 held loosely in place by a clamping frame 86. Rocker members 130, 132 allow the bearing elements to move or rock relative to the base member. The patella component has a base plate 220 and a bearing element 222 held loosely in place by a plurality of pins 228. A rocker member 232 allows the bearing element to move or rock relative to the base plate. Force transducers or sensors 150, 240 connected to computers are positioned in the provisional components 80, 85 and provide readings of the location and magnitude of the sum of the forces generated in the joint when the joint is moved through its range of motion.

13 Claims, 7 Drawing Sheets

U.S. PATENT DOCUMENTS 4,936,853 6/1990 Fabien et al. .
4,959,071 9/1990 Brown et al. .
4,986,281 1/1991 Preves et al. .
5,032,132 7/1991 Matsen, III et al. .
5,056,530 10/1991 Butler et al. .
5,080,675 1/1992 Lawes et al. .
5,197,488 3/1993 Kovecevic .................................. 128/782

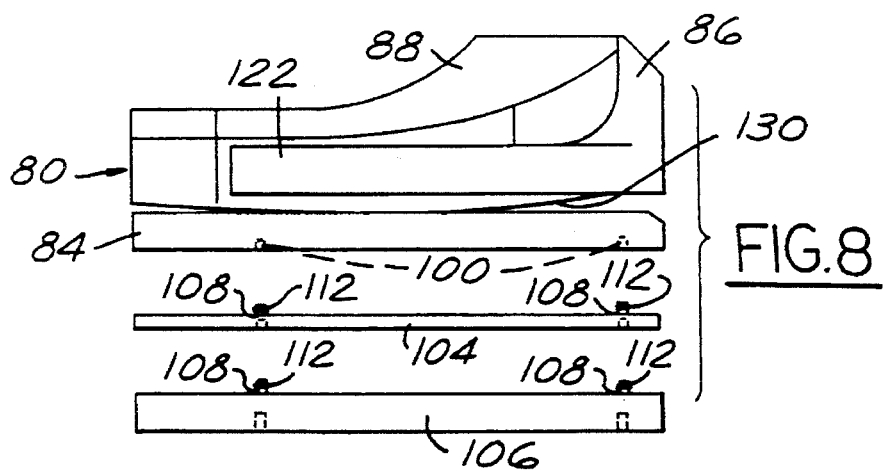
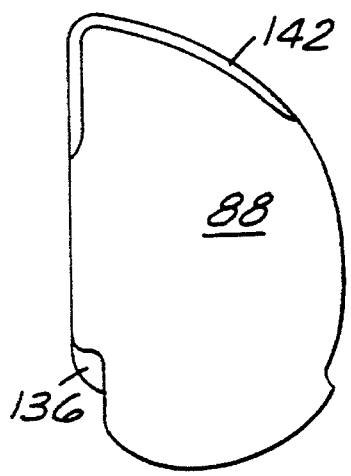
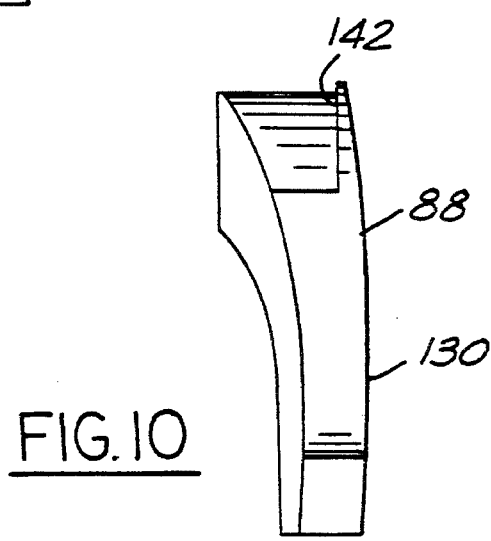
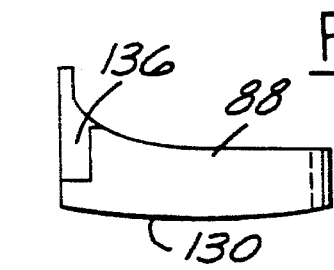
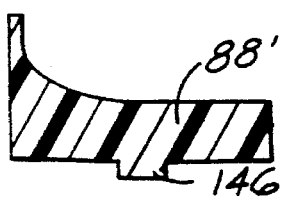
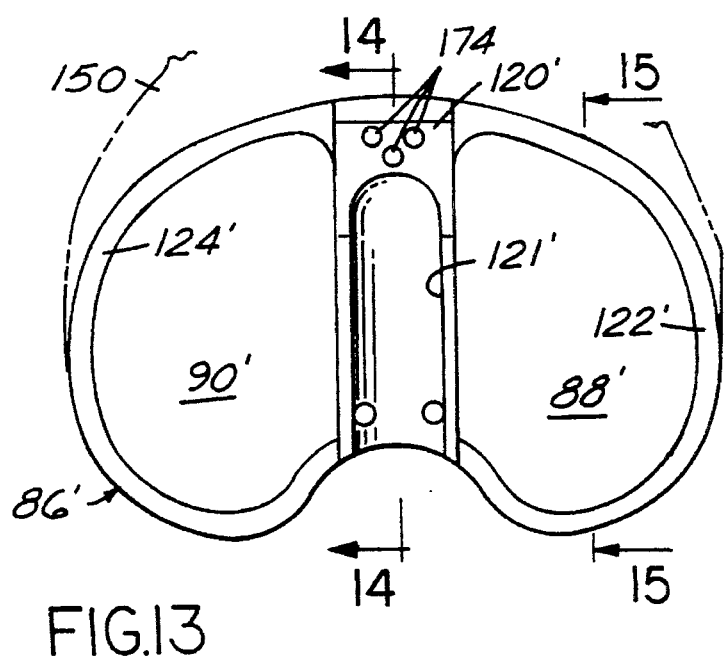

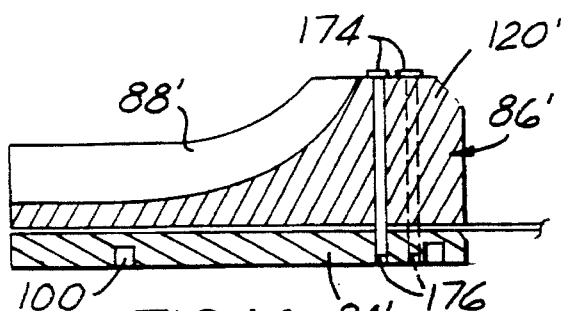
FIG.14
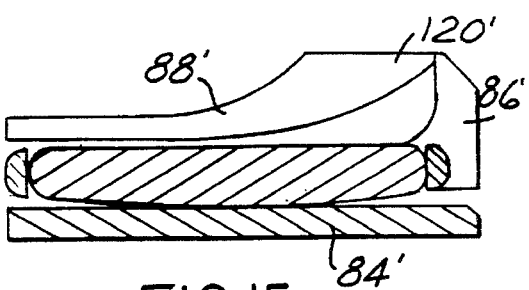
FIG.15
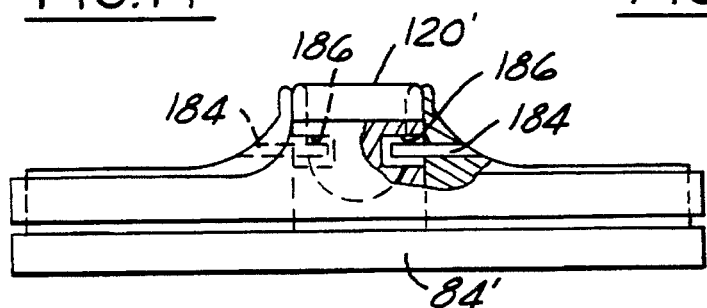
FIG.16
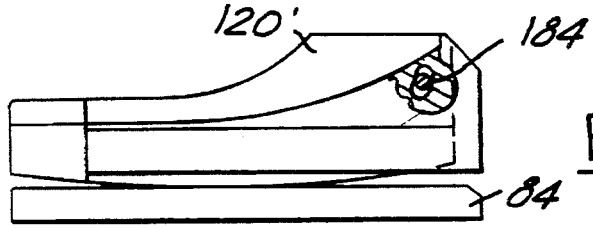
FIG.17
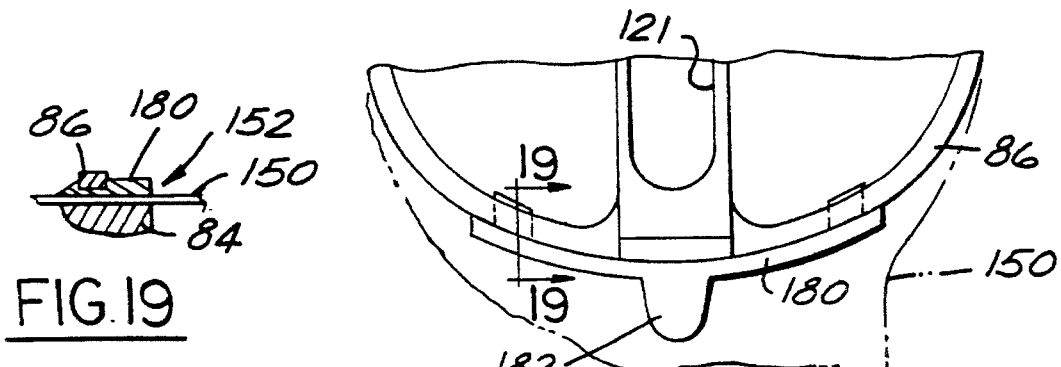
FIG.19
FIG.18
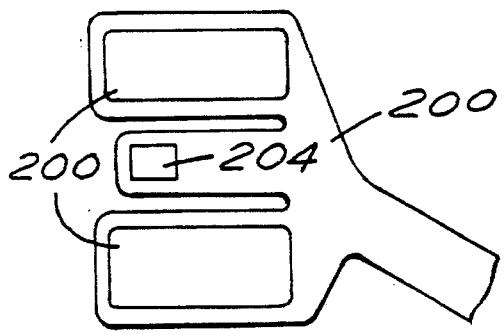
FIG.20

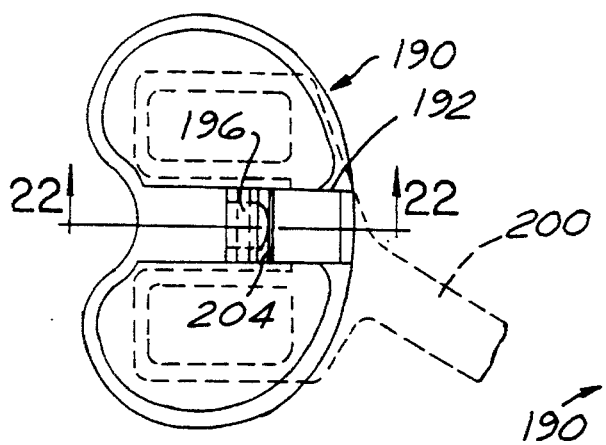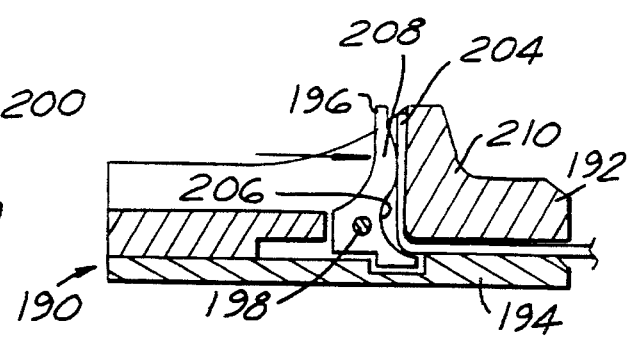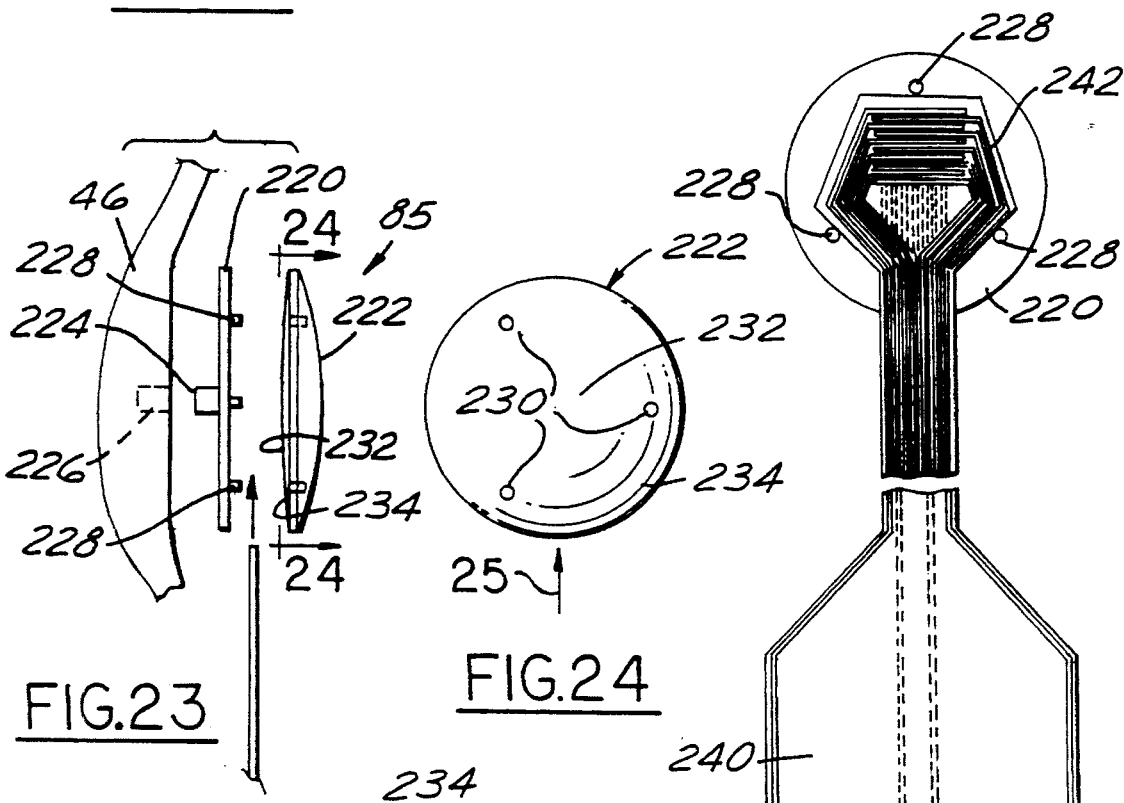

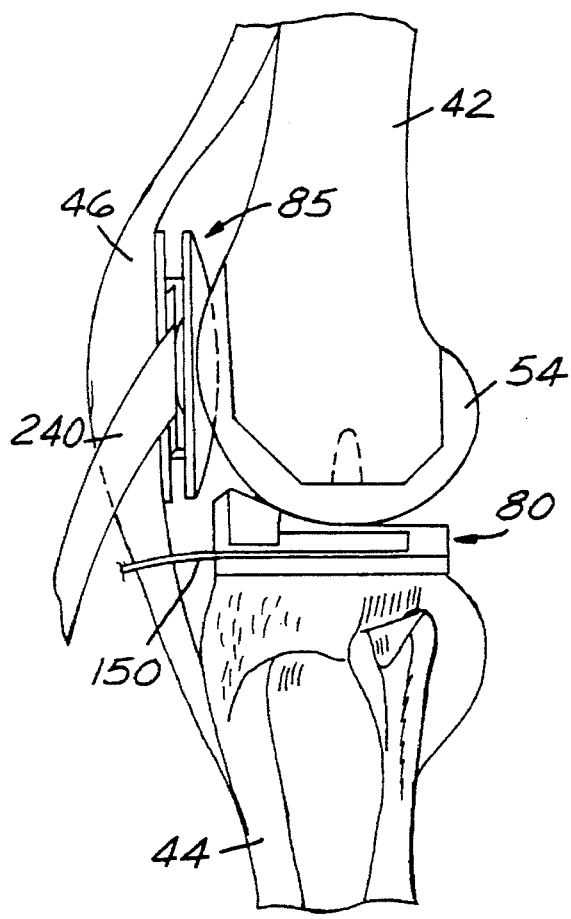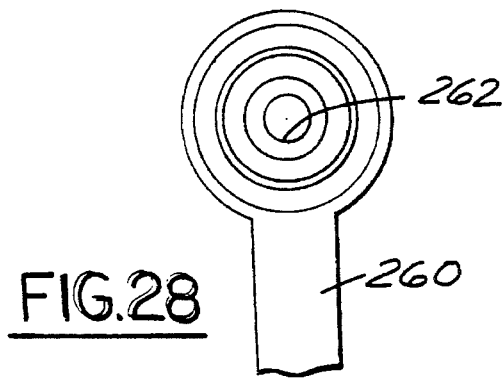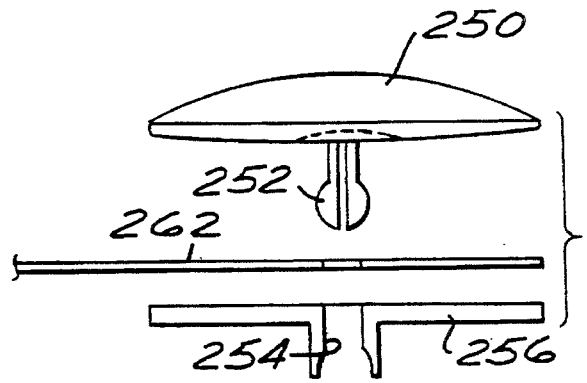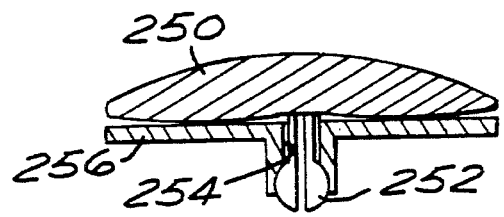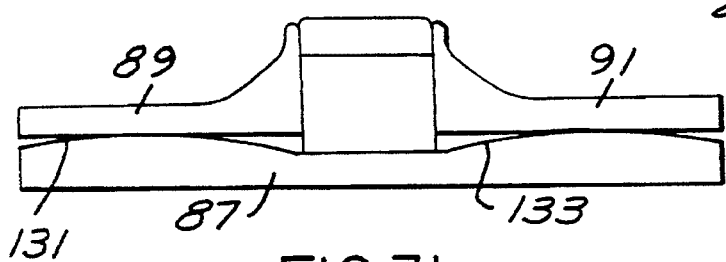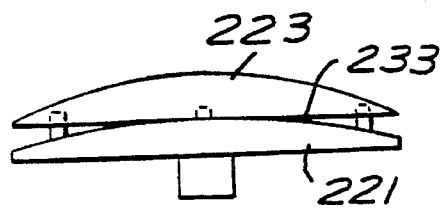
FIG. 27
FIG. 28
FIG. 29
FIG. 30
FIG. 31
FIG. 32

FORCE SENSING APPARATUS AND METHOD FOR ORTHOPAEDIC JOINT RECONSTRUCTION

TECHNICAL FIELD

This is a continuation of application Ser. No. 07/790,176, filed on Nov. 12, 1991, now abandoned.

The present invention relates to methods and devices for assessing and determining proper alignment and placement of implant components during joint reconstructive surgery. Provisional components with force transducers (sensors) are positioned in the joint and used to determine the precise forces and determine how to balance the forces in the joint.

BACKGROUND ART

In joint reconstructive surgery, it is important that the implant components be installed in correct alignment and positioned so as to produce proper motion with respect to the surrounding joint structures. For total knee arthroplasty, for example, the femoral, tibial and patella implants must all be properly installed and positioned in the knee joint and be in balance with the existing soft tissue joint support structures.

Proper alignment and placement of the implant components, as well as the proper balancing and tensioning of surrounding joint structures is imperative to the long term success of the arthroplasty. Improper alignment, placement and balancing may result in joint instability and unsatisfactory function, as well as possible increased wear rates between components.

Several methods have been used in the past for determining the proper alignment and placement of joint implant components. For example, one such method involves the visualization of alignment checks by the surgeon. As the surgeon moves the joint through its range of motion, the relative motion of the components is visualized and the implant components are placed accordingly. This method has weaknesses, however, as it is difficult to view the forced motion between the knee components with the patella reduced into its natural position. Moving the patella does not help since true motion of the components cannot be obtained unless the patella is in its natural position.

Another known method involves viewing the rollback of the femur on the tibia with the posterior cruciate ligament ("PCL") spared and in place. Again, difficulties arise in attempting to view the rollback with the patella reduced into its natural position. Several current implant designs feature dished condyles and a femoral component with a decreasing radius of curvature which make viewing of the joint contact point difficult during rollback. Yet in order to obtain satisfactory results from a PCL sparing arthroplasty it is helpful to determine the effectiveness of the PCL during rollback.

Still another known method involves determining the joint tension between the femoral and tibial components. The separation of the knee joint is viewed and felt as the knee is forced by the surgeon into varus or valgus at several degrees of flexion. A calibrated distractor, such as that shown in U.S. Pat. No. 4,501,266, is then used to apply a known force across the femoral-tibial joint and the resulting alignment is observed. The joint tension is further altered by inserting various heights of tibial provisional components and observing the resulting stability. One of the difficulties with this procedure is that it relies on the surgeon's "feel" and thus is subjective. The results of the implant procedure might vary from operation to operation and might be affected by the weight or size of the limb. The procedure also provides limited quantitative data on the joint force between the femoral and tibial components and provides limited quantitative estimates of the differences in joint contact forces between the medial and lateral condyles of the femoral component. It is also difficult with this procedure to monitor or determine the forces between the patella and femur.

The alignment and placement of the patella is determined primarily by visualization while moving the joint through a range of motion to see if it operates properly. This is affected by the choice of joint line reconstructed by the implant components and visualization does not detect the magnitude or direction of the forces in the joint. The proper joint line is often difficult to determine, however, and an improper joint line can cause excessive or insufficient joint forces between the patella and femoral components.

It is an object of the present invention to provide improved methods and devices of determining proper alignment, functioning, tensioning and positioning of joint reconstruction components.

It is another object of the present invention to provide improved methods and devices for determining the forces in the joint and thus determining the proper placement, alignment and positioning of implant components, particularly for knee joint reconstructions.

It is a further object of the present invention to provide improved methods and devices for determining femoral-tibial joint forces and relative movement by means of a provisional implant and use of force transducer mechanisms.

It is a still further object of the invention to provide a method and device for determining patella-femoral joint forces.

It is another object to provide a method and device for determining proper alignment and placement of a patella implant component through use of a patella provisional component and force transducer mechanisms.

A more specific object of the invention is a provisional component for use in knee joint reconstruction procedures with a force transducer which comprises a base member, at least one bearing element, a rocker means, and means for connecting said bearing element to said base member with said rocker means in sufficient contact with said base element that a force transducer positioned between the base member and the rocker means will be exposed to forces placed upon the bearing element during flexion of the joint.

Another more specific object of the invention is a method for assessing and determining proper alignment and placement of permanent implant components during knee joint reconstruction which comprises the steps of affixing a first permanent implant prototype on one side of a joint; preparing a plateau on another side of the joint for receiving a second permanent implant; provisionally affixing a base to the plateau and interposing a bearing element between the first permanent implant prototype and the base rockable relative to the base in response to manipulation of the joint; provisionally interposing a force sensor between the base and the bearing element adapted to generate force signals when the bearing element rocks relative to the base; manipulating said knee joint through a desired range of flexion to cause the bearing element to rock relative to the base and generate a pattern of force magnitude and location signals indicative of knee joint alignment and contact areas; making adjustments to the joint as necessary to balance the forces and assure proper alignment and positioning of the permanent implants in view of the pattern of force signals, removing the base, bearing element and force sensor from the plateau; substituting the first permanent implant for its prototype; and placing a second permanent implant on the plateau.

Still other objects, features, benefits and advantages of the present invention will become apparent from the following statement of the invention, description of the preferred embodiments, and appended claims and drawings.

DISCLOSURE OF INVENTION

The present invention meets the above-stated objects and overcomes the problems associated with earlier methods and devices for assessing and determining the proper alignment and placement of joint implant components. The invention provides a method and apparatus for measuring the forces and relative movements between the femoral and tibial provisional components as well as between the patella and femoral provisional components. The surgeon can determine the exact forces in each joint, properly balance the soft tissue support structures, and verify that the reconstructed joint line is acceptable. The invention also allows determination of the location of the contact areas between the joint components which helps show the relative motion between the components and in turn provides guidance as to the proper alignment.

In particular, a provisional component is provided which is temporarily installed on the prepared end of the tibia. This tibial component has a pair of bearing elements which are loosely held in place on the component and mate with the condyle structures of the femoral implant. A force transducer (sensor) linked to a computer terminal is positioned in a slot in the tibial component. The bearing elements include rocker elements which rest on the force sensor. The specific contact areas of the femoral component and bearing element are summed and transferred to that corresponding area of the force transducer and displayed as a point or line on the data terminal. When the joint is moved through its range of motion, the magnitude and location of the sum of the forces generated in the joint are transferred to the sensor by the bearing elements. These forces in turn are displayed on the data terminal.

The tibial component is clamped or locked onto the sensor in order to prevent relative movement during use. An adjustable clamping member can be used to hold the sensor in the slot in the tibial component. The sensor could also be held in place by a retaining clip or pins. The bearing elements also are interlocked with or pinned to the tibial component so they will not be dislodged in the joint or operating room during use. Additional plates can be attached to the tibial component to raise its height if necessary in order to have the device correspond to actual implant dimensions.

The benefits of the invention can also be achieved with an alternate provisional tibial component in which the rocker elements are situated on the tibial component instead of on the bearing elements. Similar movements and forces are developed.

Another provisional component is provided to determine the magnitude and location of forces acting on the patella. A provisional patella component is installed on the prepared posterior side of the patella and a force transducer (sensor) is used to ascertain the forces. The sensor is positioned between a base plate and bearing element which is loosely affixed to the base member. A rocker element is preferably positioned on the bearing element, although it also could be positioned on the base plate. When the patella provisional component is installed and the joint is flexed through its range of motion, the joint forces and force location are determined by the sensor and a computer data system.

The present invention can be used for improved reconstruction of any joint in which implants are used. A provisional joint component is situated in the joint and the resultant forces are monitored and displayed on the computer data system.

The present invention allows the surgeon to detect the exact force between the provisional components as well as their actual relative motion. This allows the surgeon to make the necessary adjustments to the implant position and/or soft tissue support structures to properly balance the joint. By producing a more balanced knee joint and preventing excessive joint laxity and forces, superior long-term results may develop in the form of greater range of motion, superior joint stability and decreased wear and component failure rates.

The present invention also provides a way for the surgeon to better visualize the rollback of the femoral component on the tibial component through the motion of the contact areas. The surgeon can access the function of the PCL and better determine if it should be sacrificed and substituted with an appropriate implant design.

BRIEF DESCRIPTION OF DRAWINGS

FIG. 8 depicts use of height augmentation devices with the tibial component of the present invention;

FIG. 9 is a top plan view of a bearing element of the tibial component;

FIGS. 10 and 11 are side and end plan views, respectively, of the bearing element shown in FIG. 9;

FIG. 12 depicts an alternate embodiment of a bearing element for use with the tibial component;

FIG. 13 illustrates a second embodiment of a tibial provisional component;

FIG. 14 is a cross-sectional view of the tibial component shown in FIG. 13, taken along lines 14—14 of FIG. 13;

FIG. 15 is another cross-sectional view of the tibial component shown in FIG. 13, this time taken along lines 15—15 of FIG. 13;

FIG. 16 illustrates another aspect of the alternate embodiment of tibial component for use with the present invention;

FIG. 17 is a side plan view of the tibial component shown in FIG. 16;

FIG. 18 depicts use of a retainer clip member for securing the force transducer in a tibial provisional component;

FIG. 19 is a cross-sectional view of the retainer clip member of FIG. 18, taken along lines 19—19 of FIG. 18;

FIG. 20 illustrates an alternative force transducer specially adapted for use with the tibial provisional component embodiment shown in FIGS. 21 and 22;

FIG. 21 is a top plan view of still another embodiment of a tibial provisional component for use in the present invention;

FIG. 22 is a cross-sectional view of the tibial component of FIG. 21, taken along lines 22—22 of FIG. 21;

FIG. 23 is an exploded plan view depicting the elements of the preferred patella provisional component of the present invention;

FIG. 24 is a bottom plan view of the bearing element of the patella component;

FIG. 25 is a side plan view of the bearing element shown in FIG. 24;

FIG. 26 illustrates the positioning of the patella force transducer in the base plate of the patella provisional component shown in FIG. 23;

FIG. 27 depicts concurrent use of tibial and patella provisional components in accordance with the present invention;

FIG. 28 illustrates an alternate embodiment of patella force transducer which is adapted for use with the alternate patella provisional component shown in FIGS. 29 and 30;

FIGS. 29 and 30 depict an alternate embodiment of a patella provisional component for use in the present invention; and FIGS. 31 and 32 show alternate embodiments of the provisional tibial and patella components, respectively, in which the rocker members are situated on the base members.

BEST MODE(S) FOR CARRYING OUT THE INVENTION

Figures 1, 2:
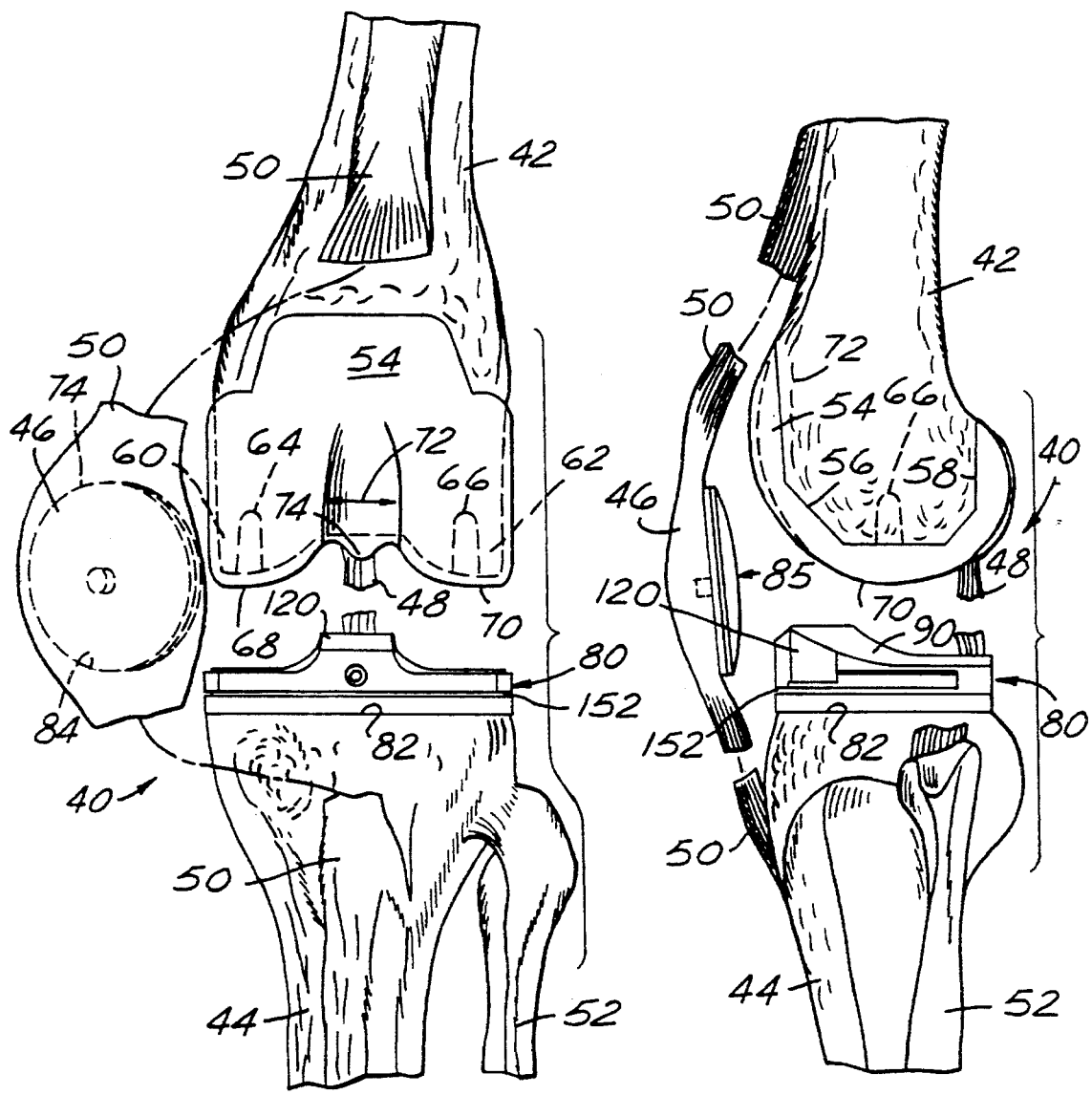
FIGS. 1 and 2 are front and side views, respectively, of a knee joint showing use of the preferred embodiment of the present invention.

FIGS. 1 and 2 illustrate the use of the preferred embodiment of the invention. The invention is adapted for use in properly aligning and placing the implant components of a knee joint reconstruction. The knee joint is generally referred to by the reference numeral 40. The joint 40 is generally formed by the femur 42, the tibia 44, the patella 46. The joint 40 is held together by muscles, ligaments and other soft tissue, most of which is not shown for reasons of clarity. FIGS. 1 and 2 do show, however, the posterior cruciate ligament ("PCL") 48 and some of the muscles and ligaments 50 which surround and support the patella. The fibula 52 is also shown.

Although the present embodiments of the invention are shown herein as being used for knee joint reconstruction, it is understood that the principles of the invention can be used to aid in the alignment and placement of implant components throughout the body, for example, in hip, elbow or shoulder joints, where significant load forces are generated.

Referring back to FIGS. 1 and 2, the components of the knee joint are shown separated and spaced apart from one another simply for convenience in describing and illustrating the invention. In actuality, the components will be closely grouped together and in contact, similar to the knee joint shown in FIG. 27.

In the joint 40 as shown in FIGS. 1 and 2, a provisional or trial femoral component 54 is shown in position on the end of the femur. The femur has been resected to fit the contours of the internal straight surfaces (e.g. 56, 58) of the femoral component 54. Holes have been drilled in the medial condyle 60 and lateral condyle 62 for receiving cylindrical posts 64 and 66 of the femoral component 54 as illustrated. Preferably, the femoral implant component 54 is the same as that shown in U.S. Pat. No. 4,959,071, the disclosure of which is hereby incorporated by reference. The femoral component 54 is preferably formed of a biologically compatible metal, such as cobalt-chromium, or a titanium alloy.

The femoral component 54 has a pair of spaced-apart downwardly extending convex bearing portions 68 and 70 which extend from the anterior side to the posterior side of the component 54. The shapes of the outer surfaces of bearing portions 68 and 70 closely approximate the shapes of the anatomical femoral condyles 60, 62 on the distal end of the femur 42. The femoral component 54 further has a generally vertically oriented patella guide recess 72 which serves as a guide for the movements of a natural or prosthetic patella.

The femoral component 54 has a central ridge or runner 74 which extends parallel to the condyles 60, 62 and protrudes into the joint. The ridge 54 is adapted to mate with a corresponding groove in the final tibial implant component and minimize anterior movement of the femoral component when the knee flexes.

As indicated, during use of the provisional tibial and patella components in accordance with the present invention, a provisional femoral component is typically utilized. This prevents the final femoral implant component from being scratched or marred in any manner prior to final implant. Once the monitoring and testing is completed with the provisional tibial component, the final femoral implant component is installed.

The tibial component 80 is a provisional device which is inserted into and positioned in the knee joint to aid in the alignment and positioning of the final tibial implant component (not shown) which is implanted after the provisional component 80 is utilized and removed. Although the final tibial implant component is not shown since it is not necessary in order to describe the present invention, the preferred form of tibial implant component is disclosed in U.S. Pat. No. 4,959,071, the disclosure of which is hereby incorporated by reference.

The provisional tibial component 80 is used after the proximal end of the tibia is resected to form a planar plateau 82. If desired, the PCL 48 can be spared. The tibial component 80 is designed to be used in the knee joint whether or not the PCL is still in place.

A provisional patellar component 85 is also provided to aid in the proper alignment and positioning of a patella implant component. The patellar component 85 is described and discussed in more detail later with respect to FIGS. 23–30.

Figures 3, 3A:
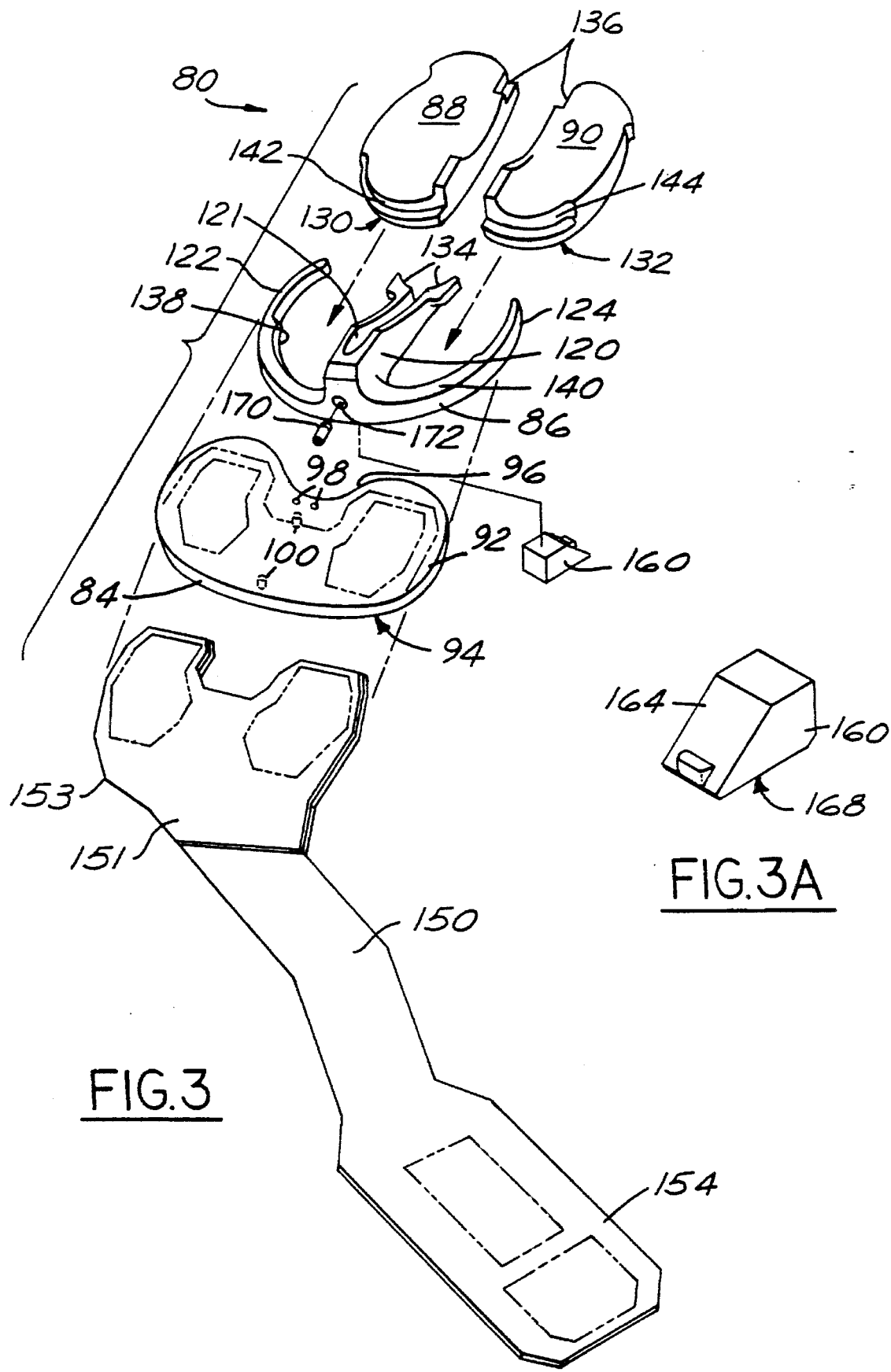
FIGS. 3 and 3A are exploded perspective views showing the primary components of the tibial provisional component of the present invention.
Figure 4:
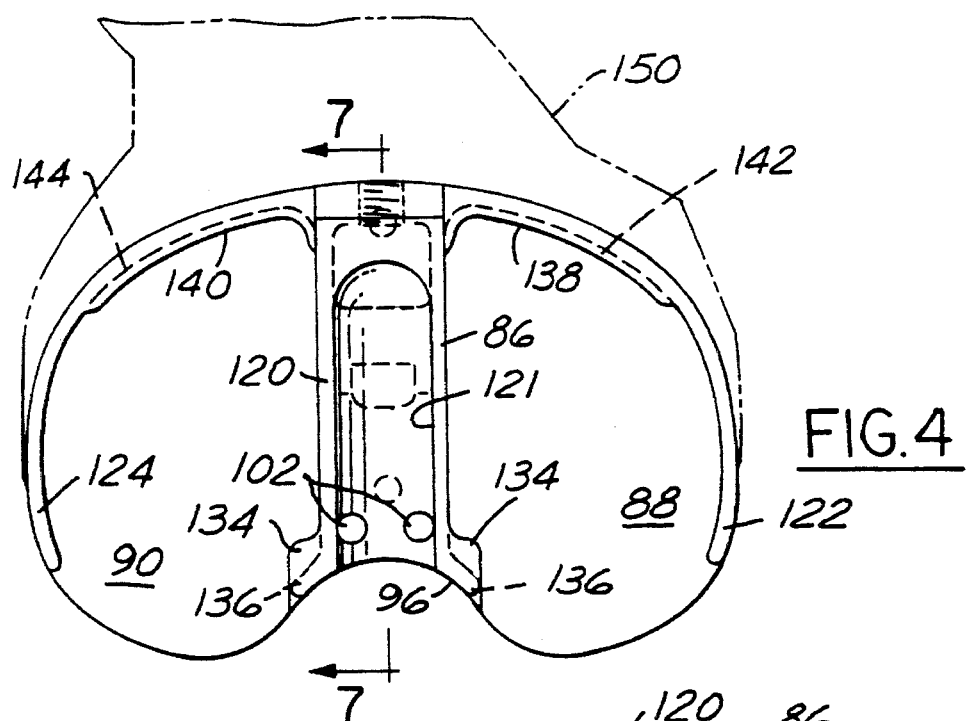
FIG. 4 is a top plan view of the tibial component shown in FIGS. 1 and 2.
Figure 5:
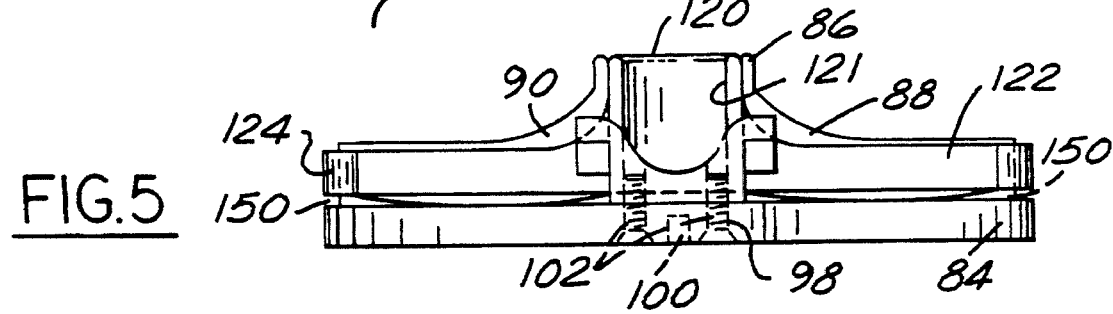
FIGS. 5 and 6 are posterior and side plan views, respectively, of the tibial component shown in FIGS. 1 and 2.
Figure 6:
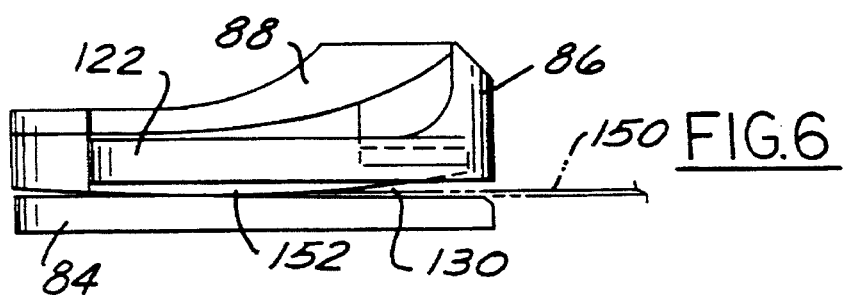

An exploded view of the tibial component 80 is shown in FIG. 3 and further details are shown in FIGS. 4–7. The component 80 generally includes a base member 84, a clamping frame 86 and a pair of bearing elements 88 and 90.

The base member has planar upper 92 and lower 94 surfaces and is provided in the general two-lobed shape shown. The surfaces are flat and smooth in order to provide a satisfactory surface for the force transducer to contact. The recessed area 96 between the two lobes provides clearance for the PCL if it is not sacrificed. The base member 84 has a pair of holes 98 which are used for fasteners 102 to secure the clamping frame 86 to the base member. The base member 84 preferably is formed of a metal material, such as stainless steel or a titanium alloy.

A pair of blind holes 100 are also provided extending into the base member from the lower surface 94. These are used to secure extension plates or shims 104, 106 (FIG. 8) to the tibial provisional component 84 if it is necessary to augment or raise the height of the component in accordance with the physical dimensions of the knee joint. Extension plates 104, 106 have the same shape and are made from the same material as base member 84. The plates 104, 106 have cylindrical posts 108, 110, respectively, which are positioned to mate within holes 100 to hold the plate and base member together. In order to assist in holding the two elements together, small rubber O-rings 112 can be positioned in grooves on the posts 108, 110. The plates 104, 106 can be made of different heights and are adapted to be fit together one on top of the other so that the tibial component 84 can be raised the requisite height. For example, extension plate 104 has a height of 2 mm, while extension plate 106 has a height of 6 mm. It is understood that a number of plates in a variety of heights can be added to adjust the tibial component to the desired position.

The clamping frame 86 has a central portion 120 and a pair of curved retaining arms 122 and 124 which are used to hold and support the bearing elements 88 and 90, respectively. The clamping frame 86 is secured to the base member 84 by screw fasteners 102 (FIGS. 5 and 7) which extend through the base member into threaded holes in the frame. The clamping frame preferably is made of the same materials as the base member, although it also could be made of anodized aluminum.

The bearing elements 88 and 90 are formed to approximate the shape of the anatomical features of the permanent tibial implant. In this regard, the upper surfaces of the elements 88 and 90 are concave or dished shaped as shown in the drawings. This allows positioning, placement and rotation of the condyles 68 and 70 of the femoral component 54 in a manner which approximates the normal movements of the original knee joint components.

The bearing elements 88 and 90 have convex curved rocker members 130, 132 on their lower surfaces. The rocker members rest on the upper surface 92 of the base member 84 and allow the bearing elements to "rock" or move angularly relative to the base member when forces or loads are applied at various parts of the upper surfaces of the bearing elements. The rocker members are preferably curved in a spherical shape as shown in FIGS. 9–11.

The bearing elements 88, 90 are preferably made from Delrin which allows some flexibility and has the ability to spread out the contact area onto the force transducer. Delrin is also autoclavable which allows the provisional tibial component to be reused in subsequent operations. Delrin further provides an acceptable coefficient of friction between itself and the femoral component which simulates the actual implant conditions. Other materials which could be used for the bearing elements include ultra-high molecular weight polyethylene (UHMWPE), stainless steel, or Celcon. In this regard, it is noted that UHMWPE is not autoclavable for reuse, but can be sterilized by other means, e.g., ethylene oxide gas sterilization or gamma radiation sterilization.

The retaining arms 122 and 124 hold the bearing elements 88 and 90 on the base member in a secure, but loose manner ("floating"). The bearing elements are held onto the base member so they will not be dislodged or fall off during movement of the provisional tibial component in the knee joint or in the operating room. At the same time, the bearing elements need to have room or space to move or rock in response to load forces being applied to them.

In order to hold the bearing elements in place on the base member, the clamping frame has a pair of outwardly extending flanges 134 which fit into mating recesses 136 on the bearing elements. In addition, the arms 122, 124 of the clamping frame have overhanging flanges 138, 140 which fit over and mate with corresponding recesses 142, 144, respectively, on the edges of the bearing elements.

An alternative rocker member for the bearing elements is shown in FIG. 12. In this embodiment, the rocker member 146 on the lower surface of bearing element 88' has an elongated ridge shape. It is also possible for the rocker member to have a cylindrical shape rather than a spherical shape with the axis of the cylinder positioned in either the medial-lateral or anterior-posterior directions of the knee joint.

It is also possible as an alternate embodiment to have the rocker members 131 and 133 positioned on the base member 87 and have the lower surfaces of the bearing elements 89 and 91 be smooth and flat. Such an embodiment is shown in FIG. 31.

A force transducer or sensor 150 is used to measure and pinpoint the loads applied in the knee joint during rotation and testing. The sensor has the shape shown in FIG. 3 and is thin (on the order of 0.010–0.020 inches in thickness). In use with the tibial component 80, the sensor 150 is inserted in the slot 152 formed between the base member 82 and the clamping frame 84 and rests between the base member 82 and the rocker members 130, 132 on the bearing elements.

The sensor preferably is a pressure sensor marketed as the "K-Scan" by Tekscan, Inc., Boston, Mass. The sensors are thin, flexible and disposable. The sensors incorporate a plurality of sensing points in a small area. The sensing points are formed by a conductive grid printing on polyester film. The insertion points are separated by a pressure sensitive semi-conductive layer which can sense the magnitude, location, timing and pressure distribution of contacts ranging from 0 psi to several thousands pounds per square inch of pressure. The Tekscan sensors are further described and illustrated in U.S. Pat. No. 4,856,993.

Preferably, the K-Scan sensors from Tekscan are modified for use with the present invention by the application of a layer of rubber latex 151 to the end 153 which is inserted in the provisional component. An additional layer of polyethylene can also be added to both sides of the end 152 of sensor 150. The additional layer or layers further spread out the contact point between the rocker member and component, and also compensate for surface irregularities.

In use, the sensors are connected at one end 154 to an adapter (not shown) which in turn electrically connects the sensor to an IBM-compatible computer terminal. The adapter is a digital to analog converter handle. Software available from Tekscan allows the forces sensed by the sensor to be displayed in various manners and formats on the computer screen. In this manner, when the provisional tibial component 80 is positioned in the knee joint and the femoral component 54 is positioned on the bearing elements 88, 90, the forces applied to the tibia 44 and component 54 during manual flexion of the joint can be immediately viewed and visualized. During the full range of flexion of the knee joint, the surgeon can determine the proper balancing of the forces and thus position and orientate the permanent implant components accordingly. The surgeon can make soft tissue adjustments in order to insure proper balancing, and also trim the bone where necessary.

As indicated, the sensor and appropriate instrumentation monitors and displays the force between the provisional components. The rocker members effectively convert multiple force vectors acting on the provisional component to a single point or line contact on the sensor. As an alternative, it is also possible to read or measure the forces simply by use of a voltage-ohm meter, although the readings would be more limited.

Figure 7:
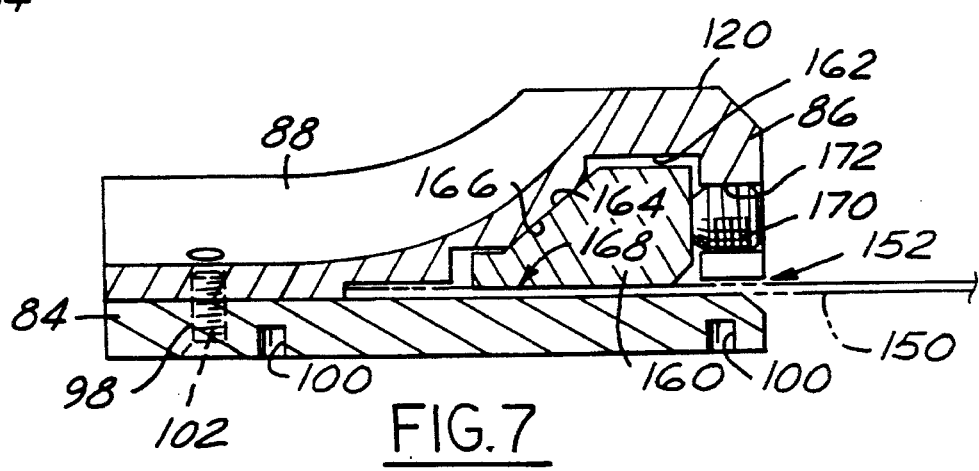
FIG. 7 is a cross-sectional view of the tibial component, taken along lines 7—7 of FIG. 4.

The sensor 150 is retained in the slot in the tibial component 80 with a clamping member 160 (see FIGS. 3, 3A and 7). The clamping member is positioned in cavity 162 in the central portion 120 of the clamping frame 86. The clamping member 160 has a sloped surface 164 which mates with correspondingly sloped surface 166 in cavity 162. When sensor 150 is positioned in tibial component 80, the base 168 of the clamping member rests on it. The clamping member is forced against the sensor to hold it in place by the tightening of stainless steel set screw 170. Screw 170 is positioned in threaded opening 172 in the clamping frame 86. When the screw is tightened against the clamping member, the mating sloped surfaces 164, 166 cause the clamping member to be forced or cammed downwardly against the sensor holding it tightly in place.

Other means or mechanisms for tightly holding or locking the sensor in place in the tibial component 84 can be used. For example, one or more pins 174 can be positioned in openings 176 which extend through the clamping frame 86 and into the base member 84' (See FIGS. 13 and 14). Three openings and pins 174 are shown in FIG. 13, but it is understood that any convenient number may be utilized. Also, for this purpose, corresponding openings (not shown) are provided in the force sensor which line up with openings 176 when the sensor is properly mated with the tibial component.

Another method for retaining the sensor 150 in the provisional tibial component is shown in FIGS. 18 and 19. In this alternate embodiment, a retaining clip 180 made of plastic, rubber or the like is forced into the slot 152 between the clamping frame 86 and the base 84 and wedged or cammed against the sensor 150. A tab 182 is provided on the retaining clip to aid in removal of the clip after the tibial component has been used.

An alternate embodiment of the provisional tibial component is shown in FIGS. 13–15. In this embodiment, the clamping frame 86' has retaining arms 122' and 124' which form complete rings around the bearing elements 88' and 90'. The base member 84' and central portion 120' of the clamping frame are similar to those described above with reference to the preferred embodiment, except that pins 174 are used to lock the sensor in place rather than a clamping member. The bearing elements 88' and 90' also are not interlocked with the retaining arms, but instead are either positioned freely in the retaining arms 122' and 124' or alternately held in place by pins 184 (See FIGS. 16 and 17). If pins 184 are used, they are positioned in enlarged openings 186 in the central portion 120'. The openings 186 are enlarged to allow the bearing elements to rock on their rounded lower surfaces (rocking members) upon application of forces in the same manner as discussed above.

The central portion 120 has a central groove 121 in its upper surface. Groove 121 is provided to mate with central ridge 74 on the femoral component 54. Rather than have a ridge on the femoral component and a mating groove on the tibial component, it is also possible to reverse the structures and have a raised ridge on the tibial component and a mating groove on the femoral component.

If an implant system is utilized in which the tibial component has a raised ridge and the femoral component has a mating recess or groove, then the embodiment of the invention as shown in FIGS. 20–22 can be utilized. In this embodiment, the provisional tibial component 190 is used to sense the force on a moving vertically oriented stabilizer in the knee joint. The clamping frame 192 is attached to the base member 194. The base member has a moving stabilizer 196 which is pivotally attached to the base member by pin 198. The sensor 200 has three fingers or sensor portions, including two outer sensor portions 202 and a central inner sensor portion 204. As the sensor is moved into position on the tibial component, the inner sensor portion 204 is forced against curved ramp 206 on stabilizer 196 and cammingly slides into a vertical orientation. During flexion of the knee joint, rocker member 208 on the pivoted stabilizer 196 presses the sensor portion 204 against the fixed stabilizer 210 and provides an output and placement of the load force against it.

The preferred provisional patella component 85 is shown in FIGS. 23–26. The patella component 85 includes a base plate 220 and a bearing element 222. After the patella 46 is resected to remove a portion of its posterior surface, the base plate 220 is positioned on it. Anchoring post 224 on base plate 220 is positioned in hole 226 formed in the patella. The base plate provides a flat smooth surface for the sensor to contact.

The base plate 220 preferably has three locating pins 228 which mate with corresponding holes 230 in the bearing element. (A different number of pins can also be utilized.) The holes 230 are made larger than the pins so that the bearing element can move or "rock" around rocker member 232. The pins locate and constrain relative sliding motion, yet allow relative rocking motion between the base plate and bearing element. Rocker member 232 is provided on lower surface 234 of the bearing element and has a large radius convex spherical dome shape.

The base plate 220 and bearing element 222 are preferably made from the same material as the base member 84 and the bearing elements 88, 90, respectively, of the tibial provisional component. In this regard, the base plate 220 is made from a metal material, such as a titanium alloy, and the bearing element 222 is made from Delrin.

The upper domed surface of the bearing element has the same radius as the implantable patella component to track in the trochlear groove of the femoral component.

Sensor 240 is used with the patella component 85 and has the relative size and shape shown in FIG. 26. Sensor 240 is similar to sensor 150 described above and preferably is made by Tekscan, Inc., Boston, Mass. The sensor 240 is similar to the "Tek-Quad" sensor made by Tekscan and has similar function and components. A layer of latex rubber is also provided on the head or end 242 of the sensor 240, together with one or two layers of polyethylene, in order to spread out the contact point between the component parts and to compensate for any irregularities.

As shown in FIG. 26, the end 242 of sensor 240 has a pentagonal shape and is positioned between the three pins 228 on the base plate 220. After the sensor is positioned on the base plate, the bearing element is installed on the pins 228 and the patella component 85 is positioned in the knee joint (as shown in FIG. 2). The opposite end 244 of the sensor is then hooked up to a computer for force determinations and readings in the same manner as discussed above with reference to sensor 150.

As the knee is flexed through the desired range of motion, the forces applied to the bearing element by the femoral component 54 show whether the patella is positioned properly in the joint, that is, whether the soft tissue is balanced and whether the joint line is properly located. In this regard, it is preferred that the new joint line of the knee implant be positioned in the same position as the original joint line for the natural knee joint.

It is possible to use and test the provisional tibial component 85 and the provisional patella component 84 separately, or it is possible to use and test them together at the same time. The concurrent use and testing of the two components is shown in FIG. 27. In this instance, the sensors 150 and 240 are both connected to the same computer so that the forces senses by both the provisional tibial and patella components can be shown and analyzed at the same time.

An alternate embodiment of the provisional patella component is shown in FIGS. 28–30. In this embodiment, the bearing element 250 has a split spring post 252 which is snap locked into opening 254 in the base plate 256. The sensor 260 has a corresponding hole 262 in the end which fits within the patella component so that the sensor will be held in place when the post is snapped into the base plate. The rocker member is a spherical "donut" situated on the surface of the bearing element adjacent the base plate.

It is also possible as an alternate embodiment to situate the rocker member 233 on the base plate 221 and have the lower surface of the bearing element 223 be flat and smooth. Such an embodiment is shown in FIG. 32.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

It is claimed:

1. A method of determining the forces acting on a provisional component used in knee joint reconstructive surgery, comprising:

installing a femoral component in a prepared knee joint to be reconstructed, said femoral component having a pair of condyle portions cooperating with a resected end of a femur and forming an articulating surface;

temporarily installing a provisional tibial component in the prepared knee joint, said provisional tibial component including a tibial member cooperating with a resected end of a tibia, and a pair of bearing elements in load bearing alignment between said tibial member and said condyle portions, said bearing elements having a pair of bearing surfaces interacting with the articulating surface, and a pair of opposite rocker surfaces, positioning a tibial force transducer between said tibial member and said pair of rocker surfaces to measure the load exerted therebetween;

flexing the knee joint through a range of motion;

monitoring the load exerted on the tibial force transducer while the joint is flexed; and adjusting the knee joint as required to achieve proper alignment and positioning of the final knee implant.

2. The method of claim 1 wherein the tibial force transducer used in the positioning step is provided with an array of load cells and said monitoring step further comprises measuring the location and magnitude of the force exerted by each of said pair of rocker surfaces on said tibial member.

3. The method of claim 2, said method further comprising:

temporarily installing a provisional patella component in the knee joint, said patella component including a patella member cooperating with a resected surface of the patella;

positioning a patella force transducer between said patella member and said resected patella surface to measure the load exerted therebetween; and monitoring the load exerted on the patella force transducer while the joint is flexed.

4. The method of claim 3 wherein the patella force transducer used in the positioning step is provided with an array of load cells and said monitoring step further comprises measuring the location and magnitude of the force exerted by said patella member on said resected patella surface.

5. The method of claim 1 wherein said step of positioning a tibial force transducer between said tibial member and said pair of rocker surfaces includes provisionally retaining said force transducer by means of a clamping member.

6. The method for accessing and determining proper alignment and placement of permanent implant components during joint reconstruction, comprising the steps of:

(1) affixing a first permanent implant prototype on one side of a joint;

(2) preparing a plateau on another side of the joint for receiving a second permanent implant;

(3) provisionally affixing a base to the plateau and interposing a bearing element between the first permanent implant prototype and the base such that the bearing element is rockable relative to the base in response to manipulation of the joint;

(4) provisionally interposing a force sensor between the base and the bearing element adapted to generate force signals when the bearing element rocks relative to the base;

(5) manipulating said joint through a desired range of flexion to cause the bearing element to rock relative to the base and generate a pattern of force magnitude and location signals indicative of joint alignment and contact areas;

(6) making adjustments to the joint as necessary to balance the forces and assure proper alignment and positioning of the permanent implants in view of the pattern of force signals;

(7) removing the base, bearing element and force sensor from the plateau;

(8) substituting a first permanent implant for its prototype; and (9) placing the second permanent implant on the plateau.

7. The method of claim 6 wherein the joint is a knee having a patella, the first permanent implant prototype is a femoral implant and the second permanent implant is a tibial implant.

8. The method of claim 7 including the further step of preparing another plateau on the patella and wherein steps (3), (4), (5), (6), (7) and (8) are performed with respect to both plateaus and step (9) includes placing the second permanent implant on one of the plateaus.

9. The method of claim 8 wherein step (5) is performed simultaneously with both bearing elements.

10. The method for assessing and determining proper alignment and placement of permanent implant components during joint reconstruction, comprising the steps of:

(1) affixing a first implant on one side of a joint;

(2) preparing a plateau on another side of the joint for receiving a second permanent implant;

(3) provisionally affixing a base to the plateau and interposing a bearing element between the first implant and the base such that the bearing element is rockable relative to the base in response to manipulation of the joint;

(4) provisionally interposing a force sensor between the base and the bearing element adapted to generate force signals when the bearing element rocks relative to the base;

(5) manipulating said joint through a desired range of flexion to cause the bearing element to rock relative to the base and generate a pattern of force magnitude and location signals indicative of joint alignment and contact areas;

(6) making adjustments to the joint as necessary to balance the forces and assure proper alignment and positioning of the implants in view of the pattern of force signals;

(7) removing the base, bearing element and force sensor from the plateau; and (8) placing the second permanent implant on the plateau.

11. The method of claim 10 wherein the joint is a knee having a patella, the first implant is a femoral implant and the second permanent implant is a tibial implant.

12. The method of claim 11 including the further step of preparing another plateau on the patella and wherein steps (3), (4), (5), (6) and (7) are performed with respect to both plateaus and step (8) includes placing the second permanent implant on one of the plateaus.

13. The method of claim 10 wherein said step of provisionally interposing a force sensor between the base and the bearing element includes retaining said force sensor by means of a clamping member.

* * * * *